(12) United States Patent
Ikoma

(10) Patent No.: US 6,435,399 B2
(45) Date of Patent: Aug. 20, 2002

(54) METHOD OF CHECKING WIREBOND CONDITION

(75) Inventor: Kazuya Ikoma, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 0 days.

(21) Appl. No.: 09/817,587

(22) Filed: Mar. 26, 2001

Related U.S. Application Data

(62) Division of application No. 09/326,833, filed on Jun. 7, 1999, now Pat. No. 6,237,833.

(30) Foreign Application Priority Data

Jun. 15, 1998 (JP) ............................................. 10-167050
Jun. 15, 1998 (JP) ............................................. 10-167051

(51) Int. Cl.[7] ............................. H01L 21/60; G01N 3/08
(52) U.S. Cl. .................... 228/104; 228/180.5; 228/102; 73/827
(58) Field of Search ................................ 228/102, 103, 228/104, 105, 180.5; 73/827; 219/85.18; 324/537

(56) References Cited

U.S. PATENT DOCUMENTS 4,984,730 A * 1/1991 Gobel et al. ................. 228/1.1
5,314,105 A * 5/1994 Farassat ....................... 228/102
5,370,300 A   12/1994 Okumura
5,570,012 A * 10/1996 Orense ...................... 324/158.1
5,591,920 A *  1/1997 Price et al. ................... 228/4.5
5,686,670 A   11/1997 Vanderlip
5,712,570 A *  1/1998 Heo et al. .................... 324/537
5,894,981 A *  4/1999 Kelly ........................... 228/104
6,164,518 A * 12/2000 Mochida et al. ............. 228/102
6,206,266 B1 *  3/2001 Takahashi et al. ........... 228/102
6,305,594 B1 * 10/2001 Mochida et al. ............ 228/180.5

* cited by examiner

Primary Examiner—Tom Dunn
Assistant Examiner—Colleen P Cooke
(74) Attorney, Agent, or Firm—Merchant & Gould P.C.

(57) ABSTRACT

A method of checking a wirebond condition is provided, wherein the wirebond condition results from the bonding of a conductive wire to an object such as a semiconductor chip and a lead. The wire is guided by a bonding tool. According to the checking method, first, a first position of the bonding tool is detected when the bonding of the wire is completed. Then, a pulling force, which is small enough to prevent breakage of the wire, is applied to the wire. In this state, a second position of the bonding tool is detected. Finally, the first and the second positions of the bonding tool are compared with each other.

7 Claims, 6 Drawing Sheets

METHOD OF CHECKING WIREBOND CONDITION

This application is a divisional of application Ser. No. 09/326,833, filed Jun. 7, 1999, now U.S. Pat. No. 6,237,833 which application(s) are incorporated herein by reference.

BACKGROUND OF THE INVENTION

1. Field of the Invention

The present invention relates to a method of checking a wirebond condition. In particular, the present invention relates to a method of checking a wirebond condition that is advantageously used for determining whether or not a metal wire is properly fixed to an object such as a semiconductor chip or a lead terminal.

2. Description of the Related Art

An example of the conventionally well-known wire-bonding techniques for electrically connecting two elements (such as a semiconductor chip and a lead) is a ball-bonding method. A typical ball-bonding operation using a bonding tool called "capillary" may be performed in the following manner.

First, a lower tip of a metal wire extending vertically through a bonding tool is melted into a ball. Then, the bonding tool is lowered toward a semiconductor chip to bring the ball-like end of the wire into contact with the semiconductor chip. Under a predetermined squeezing force, the ball-like end of the wire will be deformed between the bonding tool and the semiconductor chip. In this state, ultrasonic vibrations are applied to the bonding tool for a certain period of time. As a result, the lower end of the wire will be fixed to the semiconductor chip.

Though having many advantages, the conventional wire-bonding technique is disadvantageous in the following points.

It is now assumed that the semiconductor chip is mounted on a center pad (called "island") of a metal lead frame which in turn is carried by a flat supporting base. In such an instance, if the lead frame is not flat but warped, the central pad together with the semiconductor chip may be raised above the supporting base. When a wire-bonding operation is performed to such a raised semiconductor chip, the wire may fail to be firmly attached to the semiconductor chip.

Conventionally, the checking of wirebond condition is performed after a wire-bonding operation (that is, the wirebond condition checking is additionally performed separately from the wire-bonding operation). In this manner, however, the overall process for producing semiconductor devices tends to become time-consuming. Further, in practice, all of the semiconductor devices in the making are not subjected to the checking of wirebond condition (i.e., only arbitrarily selected ones are examined). Thus, conventionally, a certain number of defective semiconductor devices may disadvantageously be subjected to a second wire-bonding operation (or any other subsequent procedure) together with non-defective semiconductor devices.

SUMMARY OF THE INVENTION

It is, therefore, an object of the present invention is to provide a method of checking a wirebond condition which eliminates or reduces the above-described problems.

According to a first aspect of the present invention, there is provided a method of checking a wirebond condition produced by bonding a conductive wire to an object, the wire being guided by a bonding tool, the method comprising the steps of:

detecting a first position of the bonding tool when the bonding of the wire is completed;

applying a pulling force to the wire, the pulling force being small enough to prevent breakage of the wire;

detecting a second position of the bonding tool while the pulling force is being applied to the wire; and comparing the first and the second positions of the bonding tool with each other.

With such an arrangement, it is possible to know whether the bonding of the wire to the object is properly performed or not simply by comparing the first and the second positions of the bonding tool. Thus, there is no need to perform the checking of the wirebond condition separately from the wire-bonding operation.

Preferably, the above method further comprises the step of sounding an alarm when the first and the second positions of the bonding tool differ from each other.

Instead of or in addition to the above alarm-sounding step, the checking method may comprise the step of canceling a subsequent bonding operation when the first and the second positions of the bonding tool differ from each other.

According to a second aspect of the present invention, there is provided a method of checking a wirebond condition produced by bonding a conductive wire to an object, the method comprising the steps of:

detecting a first position of the object when the wire is brought into contact with the object;

detecting a second position of the object when the bonding of the wire is completed;

calculating a difference between the first and the second positions of the object; and comparing the calculated difference with a predetermined value.

With such an arrangement, it is possible to know whether the bonding of the wire is properly performed or not simply by comparing the calculated difference with a predetermined value. The predetermined value may be obtained by performing an experiment.

Preferably, the above method further comprises the step of sounding an alarm when the calculated difference is greater than the predetermined value.

Instead of or in addition to the above alarm-sounding step, the checking method may further comprise the step of canceling a subsequent bonding operation when the calculated difference is greater than the predetermined value.

In a preferred embodiment, the wire is guided by a bonding tool through which the wire extends.

The detecting of the first and the second positions of the object may be performed based on detection of positions of the bonding tool.

Other objects, features and advantages of the present invention will become clearer from the detailed description of preferred embodiments given below with reference to the accompanying drawings.

DETAILED DESCRIPTION OF THE PREFERRED EMBODIMENTS

The preferred embodiments of the present invention will be described below with reference to the accompanying drawings.

Figure 1:
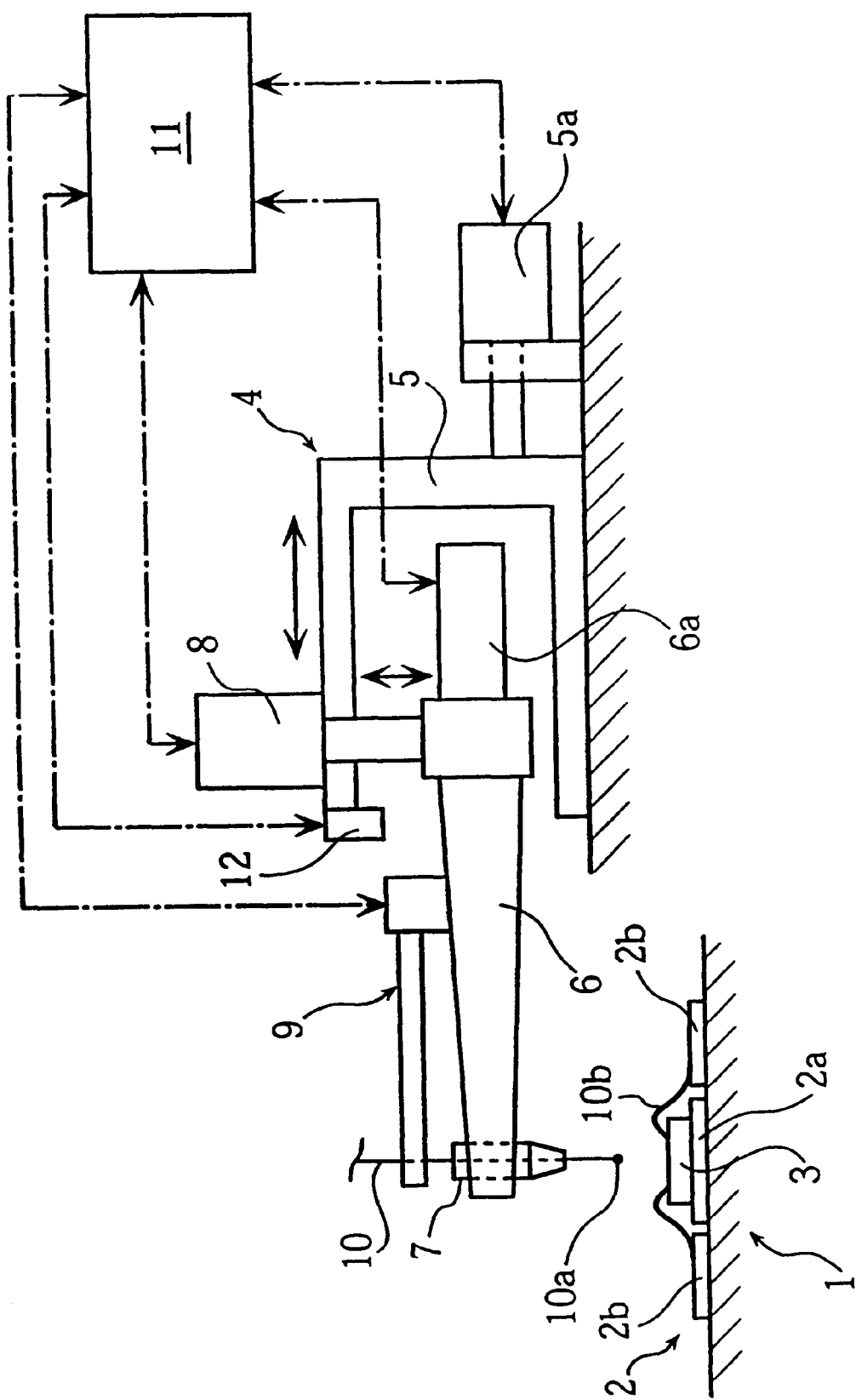
FIG. 1 is a schematic view showing a wire-bonding system according to a first embodiment of the present invention.
Figure 2:
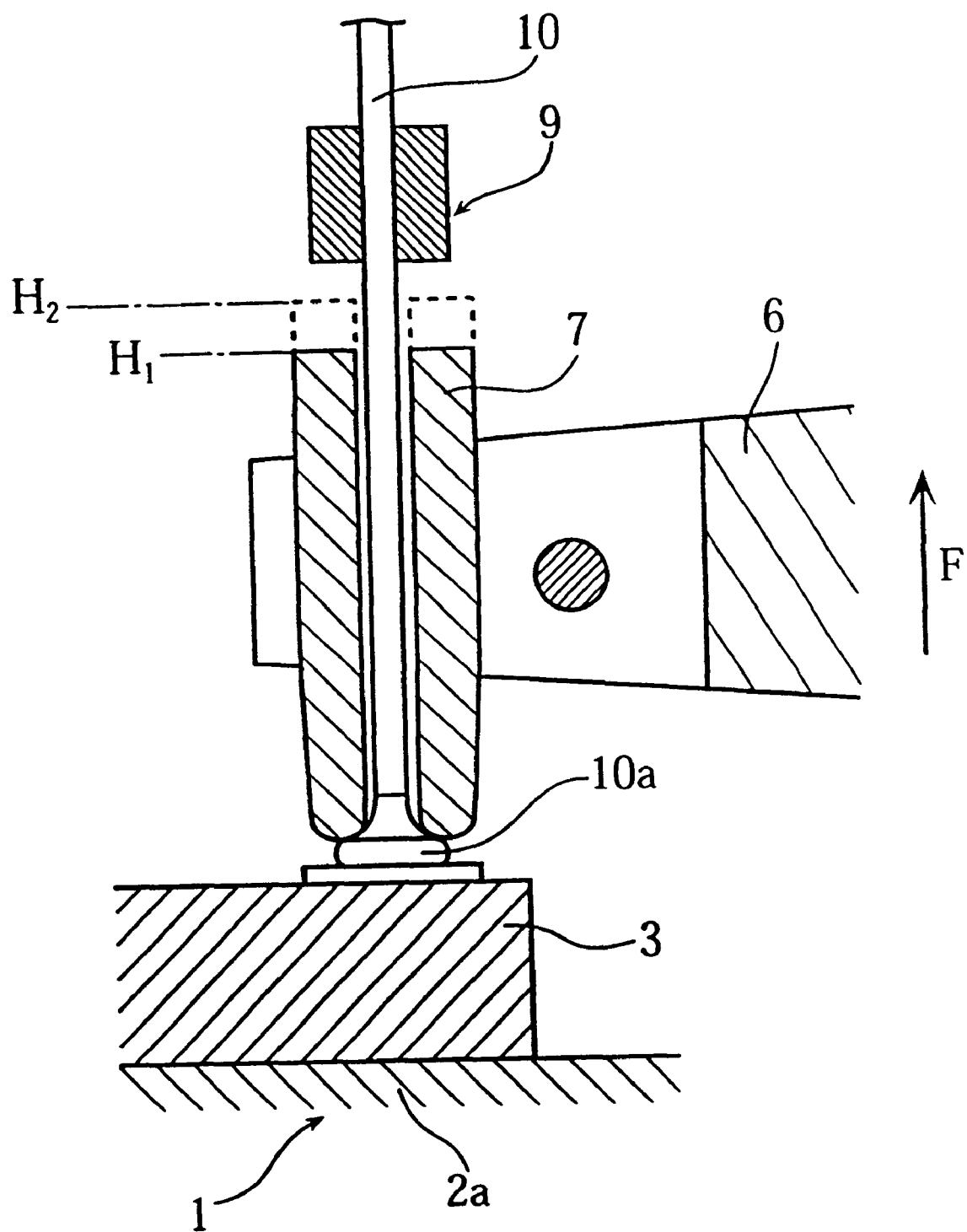
FIG. 2 is an enlarged view showing principal parts of the wire-bonding system of the first embodiment.

Reference is first made to FIGS. 1 and 2 which illustrate a wire-bonding system according to a first embodiment of the present invention. As shown in FIG. 1, the illustrated system includes a supporting base 1 incorporating a heater (not shown), a bonding apparatus 4 and a control circuit 11 for controlling the operation of the bonding apparatus 4.

The supporting base 1 supports a lead frame 2. As shown in FIG. 1, the lead frame 2 is provided with a plurality of islands 2a (only one is shown) and leads 2b. A semiconductor chip 3 is mounted on the island 2a.

The bonding apparatus 4 includes a carrier frame 5 and a horn 6. The carrier frame 5 is horizontally moved by a first actuator 5a. On the other hand, the horn 6 is vertically moved by a second actuator 8 mounted on the carrier frame 5. The horn 6 is provided at its free end with a bonding tool 7 and at its base end with an ultrasonic vibrator 6a. The bonding tool 7 is formed with a through hole for allowing passage of metal wire 10. The wire 10 may be made of gold or aluminum for example. The horn 6 supports a clamping member 9 which is arranged to releasably clamp the wire 10.

The bonding apparatus 4, which is controlled by the control circuit 11, is useful for electrically connecting the semiconductor chip 3 to the leads 2b via bonding wires 10b. Detailed explanation will be given below.

First, as shown in FIG. 1, the lower tip of the metal wire 10 is melted into a ball portion 10a by electric discharge for example. Then, the bonding tool 7 is lowered to bring the ball portion 10a into contact with the semiconductor chip 3. At this time, as shown in FIG. 2, the ball portion 10a is squeezed between the bonding tool 7 and the semiconductor chip 3 under a predetermined load.

In the state shown in FIG. 2, the ultrasonic vibrator 6a is actuated for a predetermined period of time to generate ultrasonic vibrations. These vibrations are transmitted to the bonding tool 7 via the horn 6, thereby causing the bonding tool 7 to vibrate. Then, the ball portion 10a vibrated together with the bonding tool 7 will be fixed to the semiconductor chip 3 (a first bonding procedure).

After the metal wire 10 is fixed to the semiconductor chip 3, the height H1 of the bonding tool 7 (that will be referred to as "first height" below) is detected by a sensor 12 which is included in the bonding apparatus 4 (see FIG. 1). Then, under the control of the controlling circuit 11, the clamping member 9 is actuated to clamp the metal wire 10 so that no relative movement will be made between the clamping member 9 and the metal wire 10. In this state, the horn 6 receives an upward force F from the second actuator 8. The strength of the upward force F is so adjusted that the upward force F will not break the metal wire 10. While the horn 6 is being urged upwardly, the height H2 of the bonding tool 7 (which height will be referred to as "second height" below) is detected by the sensor 12.

If the first bonding is properly performed, the metal wire 10 will not be detached from the semiconductor chip 3 upon application of the upward force F. Thus, in this case, the detected first and second heights H1, H2 should be equal (or substantially equal) to each other.

On the other hand, if the first bonding is not performed properly, the metal wire 10 will be detached partially or completely from the semiconductor chip 3 upon the upward force application. In this case, the second height H2 is greater than the first height H1.

As seen from the above description, when the first bonding procedure has not been properly performed, a certain difference is observed between the first and the second heights H1, H2. On the other hand, when the first bonding procedure has been properly performed, substantially no difference is observed between the first and the second heights H1, H2. Thus, according to the present invention, whether the first bonding has been properly performed or not can be known by simply comparing the first and the second heights H1, H2.

Figure 3:
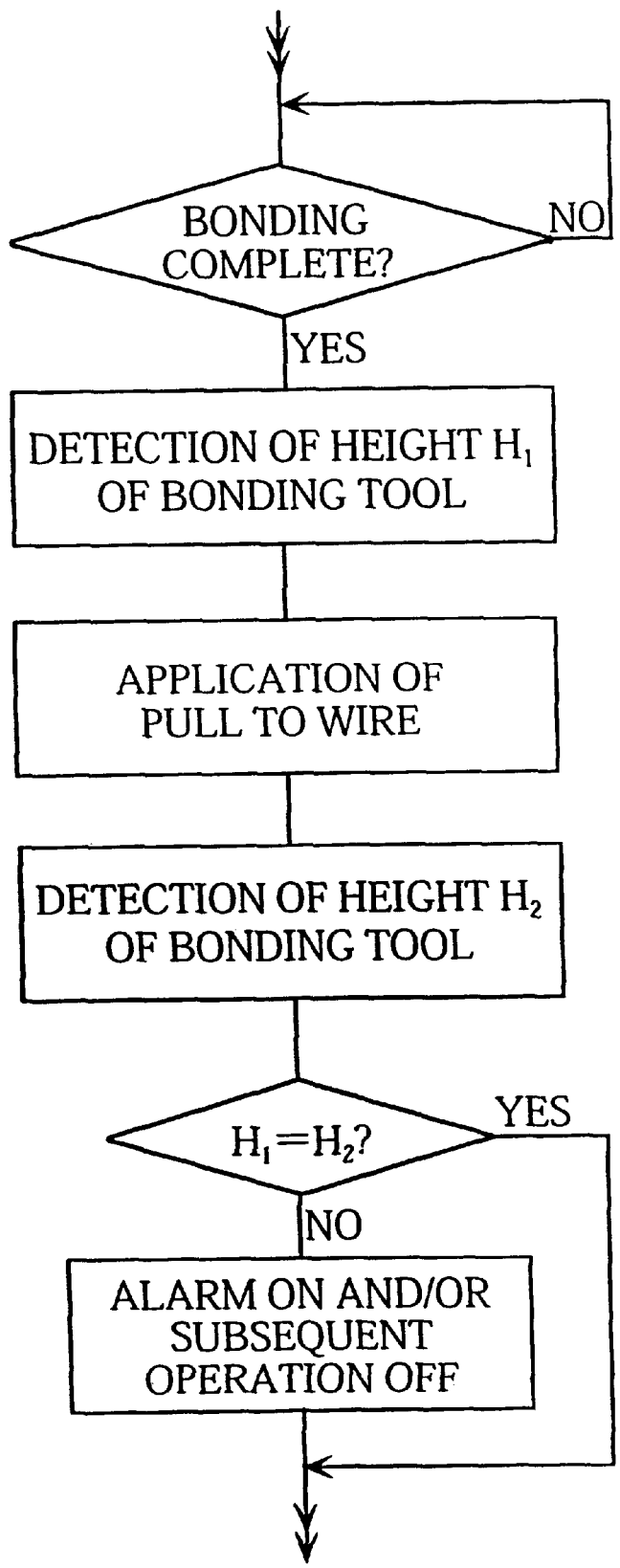
FIG. 3 is a flow chart showing principal steps of an operation performed by the wire-bonding system of the first embodiment.

When the first bonding procedure has been found unsuccessful, an alarming sound may be generated and/or the second bonding procedure may be canceled. (See also FIG. 3.) In this manner, it is possible to prevent a defective semiconductor device in the making from being subjected to another processing.

Conversely, when the first bonding has been found successful, the semiconductor device in the making will be subjected to the second bonding procedure, as will be described below.

First, under the control of the control circuit 11, the clamping member 9 releases the metal wire 10 so that the wire 10 is moved freely relative to the clamping member 9. In this state, the bonding tool 7 is lifted to a predetermined height by the second actuator 8. Then, the carrier frame 5 is moved horizontally (e.g. in the right in FIG. 1). to bring the bonding tool 7 to a position above a selected lead 2b. Thereafter, the bonding tool 7 is lowered to bring the metal wire 10 into contact with the selected lead 2b. In this manner, the metal wire 10 is squeezed between the bonding tool 7 and the selected lead 2b under a predetermined load.

Then, the ultrasonic vibrator 6a is actuated for a predetermined period of time to provide the bonding tool 7 with ultrasonic vibrations. As a result, the metal wire 10 is fixed to the selected lead 2b (a second bonding procedure). Finally, the bonding tool 7 is raised away from the selected lead 2b, while the clamping member 9 is clamping the metal wire 10. As a result, the metal wire 10 will be severed to be separated from the portion bonded to the selected lead 2b. In this manner, as shown in FIG. 1, a separate piece of bonding wire 10b is obtained.

In the above embodiment, measurement of height is performed for the bonding tool 7. However, this is not limitative and the detection of height may be performed for other parts such as the clamping member 9 or the horn 6.

Figure 4:
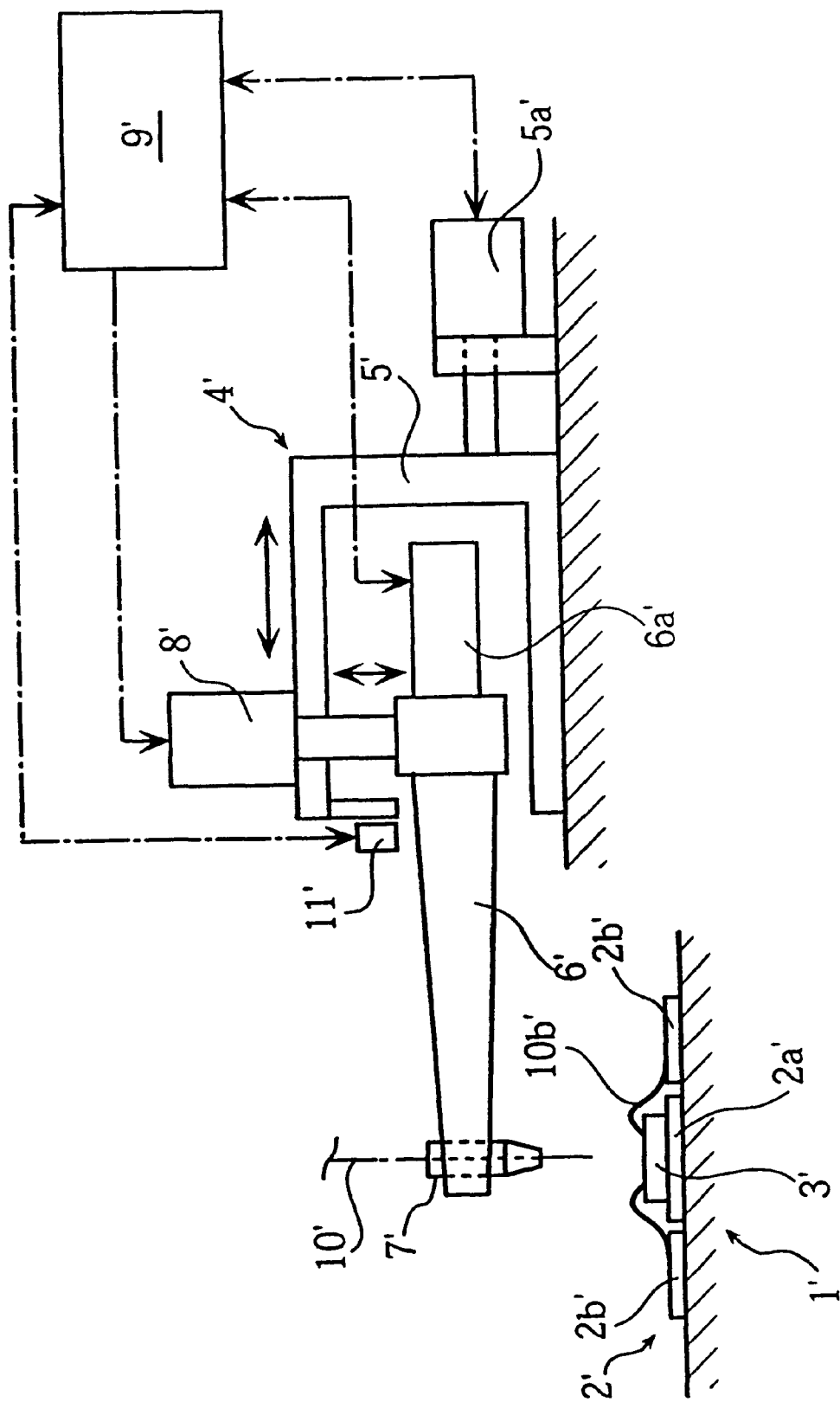
FIG. 4 is a schematic view showing a wire-bonding system according to a second embodiment of the present invention.

Reference will now be made to FIGS. 4–7 which illustrate a wire-bonding system according to a second embodiment of the present invention. As shown in FIG. 4, the wire-bonding system of this embodiment includes a supporting base 1' incorporating a heater (not shown), a bonding apparatus 4' and a control circuit 9' for controlling the operation of the bonding apparatus 4'.

The base 1' supports a lead frame 2' which is provided with a plurality of islands 2a' (only one is shown) and leads 2b'. A semiconductor chip 3' is mounted on the island 2a'.

The bonding apparatus 4' includes a carrier frame 5' and a horn 6'. The carrier frame 5' is moved horizontally by a first actuator 5a'. On the other hand, the horn 6' is moved vertically by a second actuator 8' mounted on the carrier frame 5'. The horn 6' is provided at its free end with a bonding tool 7' and at its base end with an ultrasonic vibrator 6a'. The bonding tool 7' is formed with a through hole for allowing passage of metal wire 10'. The wire 10' may be made of gold or aluminum for example.

The bonding apparatus 4' is operated in the following manner under the control of the control circuit 9'.

First, the lower tip of the metal wire 10' is melted into a ball portion 10a' by e.g. electric discharge. Then, the bonding tool 7' is lowered to bring the ball portion 10a' into contact with the semiconductor chip 3' (see (A) in FIG. 5). Then the ball portion 10a' is squeezed between the bonding tool 7' and the semiconductor chip 3' under a predetermined load (see (B) in FIG. 5). At this stage, as shown in FIG. 5, the ball portion 10a' is squeezed between the bonding tool 7' and the semiconductor chip 3' under a predetermined load.

While the ball portion 10a' is held in the squeezed state, the ultrasonic vibrator 6a' is actuated for a predetermined period of time to provide the bonding tool 7' with ultrasonic vibrations. As a result, the ball portion 10a' will be fixed to the semiconductor chip 3' (a first bonding procedure).

Figure 5:
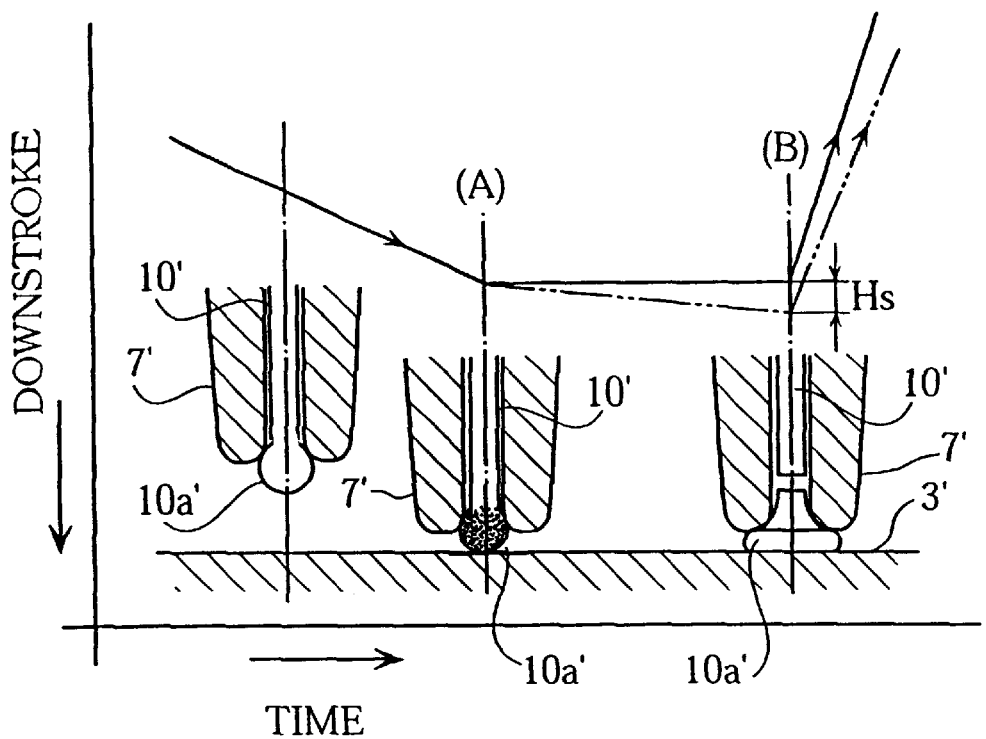
FIG. 5 illustrates a relation between time and a bonding tool used for performing a first bonding.

Then, the bonding tool 7' is lifted to a predetermined height by the second actuator 8' ((B) in FIG. 5). During the rise of the bonding tool 7', the metal wire 10' is freely paid out from the bonding tool 7'.

Then, the carrier frame 5' is moved horizontally (e.g. in the right in FIG. 4) to bring the bonding tool 7' to a position above a selected lead 2b'. Thereafter, the bonding tool 7' is lowered to bring the metal wire 10' into contact with the selected lead 2b' (see (C) in FIG. 6). Then the metal wire 10' is squeezed between the bonding tool 7' and the selected lead 2b' under a predetermined load (see (D) in FIG. 6).

While the metal wire 10' is held in the squeezed state, the ultrasonic vibrator 6a' is actuated for a predetermined period of time to provide the bonding tool 7' with ultrasonic vibrations. Thus, the metal wire 10' will be fixed to the selected lead 2b' (a second bonding procedure).

Finally, the bonding tool 7' is raised away from the selected lead 2b', while the metal wire 10 is clamped by a suitable clamping mechanism. As a result, the metal wire 10' will be severed without using an additional cutting means. In this manner, as shown in FIG. 4, a separate piece of bonding wire 10b' is obtained.

Figure 6:
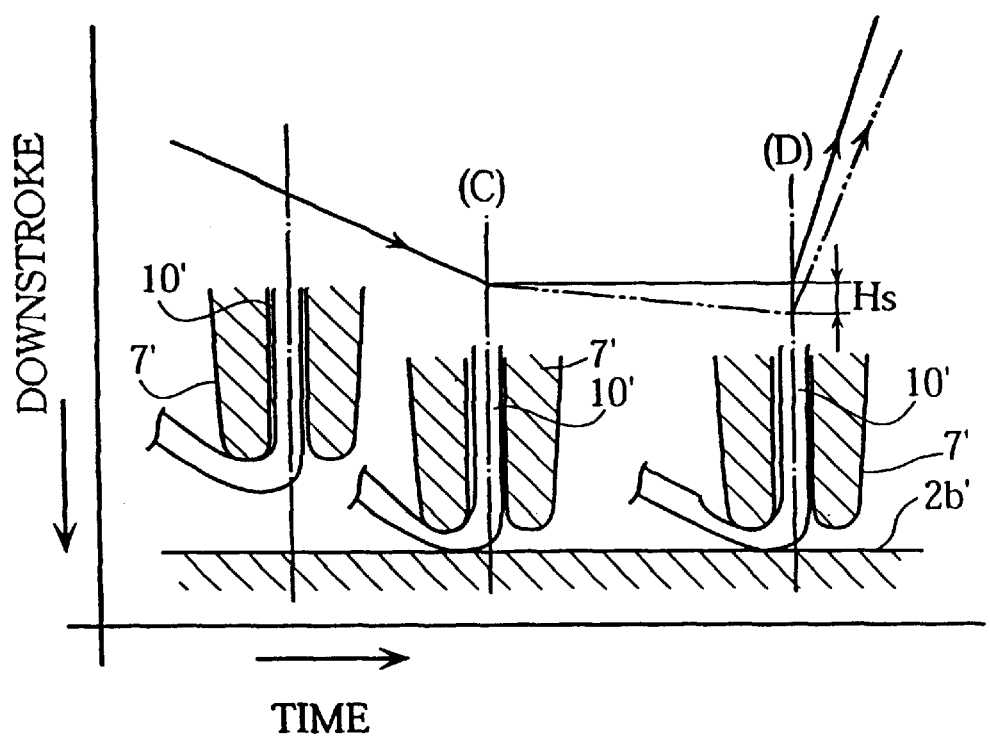
FIG. 6 illustrates a relation between time and the bonding tool used for performing a second bonding.

The advantages of the wire-bonding system according to the second embodiment will now be described below with reference to FIGS. 5 and 6.

It is assumed that the lead frame 2' placed on the supporting base 1' is not completely flat but partially warped. Then, an island 2a' carrying a semiconductor chip 3' may be raised from the surface of the supporting base 1' by a distance Hs. Under these circumstances, when the bonding tool 7' is lowered for bringing the ball portion 10a' into pressing contact with the chip 3', the chip 3' is pressed down by the distance Hs, as illustrated by double-dot chain lines in FIG. 5. (Such a downward displacement may also be observed in performing a second bonding, as shown in FIG. 6.)

When the chip 3' is lowered as stated above, the ball portion 10a' and the chip 3' contacting therewith may fail to be properly vibrated. In such an instance, the ball portion 10a' and the chip 3' may not be attached firmly to each other.

According to the second embodiment, however, the occurrence of such an undesirable wirebond condition is easily detected in the following manner.

As shown in FIG. 4, the wire-bonding system of the second embodiment is provided with a sensor 11' which is supported by the bonding apparatus 4'. The sensor 11' is arranged to detect the height (vertical position) of the horn 6'. As illustrated, the sensor 11' is associated with the control circuit 9' to be controlled thereby. In such an arrangement, the height of the bonding tool 7' is. indirectly detected through measurement of the height of the horn 6'. (Instead, the height of the semiconductor chip 3' may directly be detected by a suitable sensor.)

Figure 7:
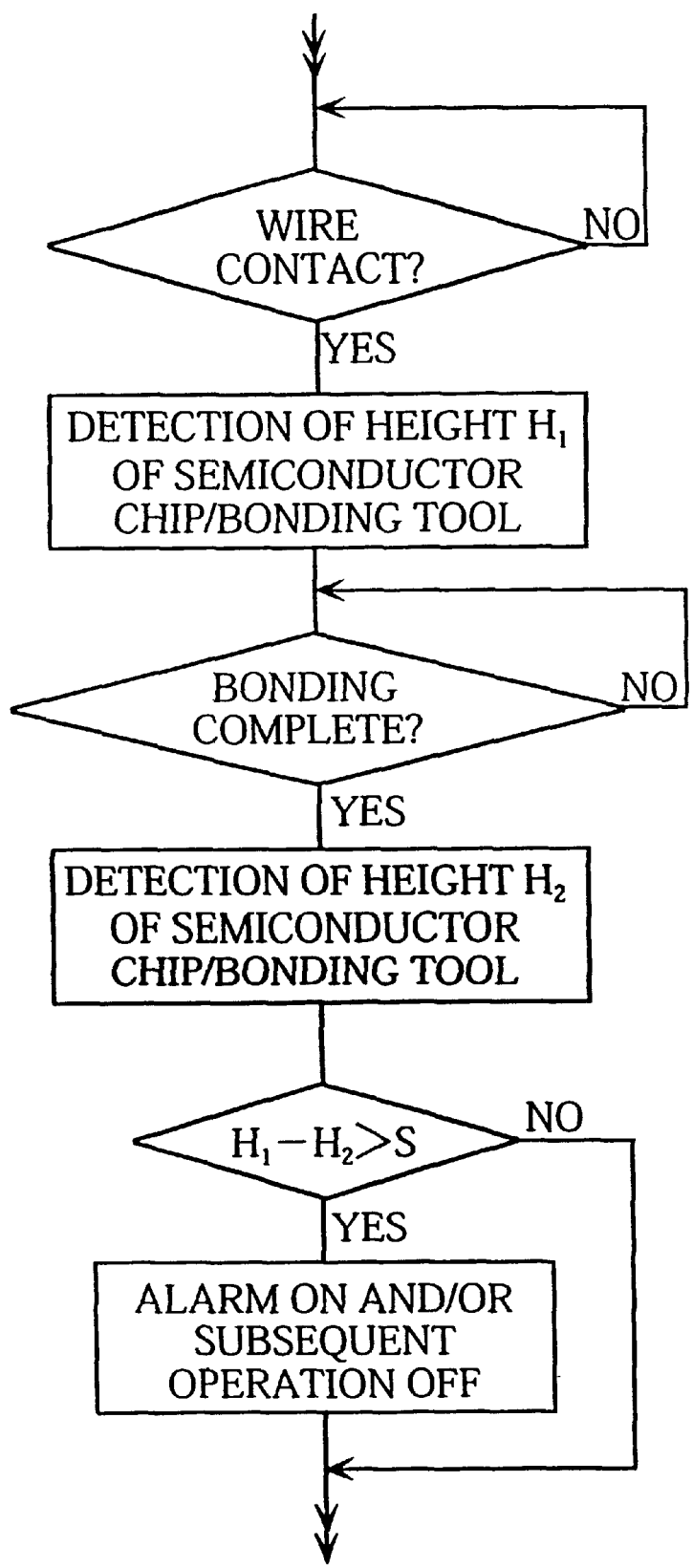
FIG. 7 is a flow chart showing principal steps of an operation performed by the wire-bonding system of the second embodiment.

Specifically, when the ball portion 10a' is first brought into contact with the semiconductor chip 3' (see (A) in FIG. 5), an initial or first height H1 of the chip 3' or the bonding tool 7' is detected (see also FIG. 7). After that, a second height H2 of the chip 3' or the bonding tool 7' is detected at the end of the first bonding operation (see (B) in FIG. 5). Then, the difference between the first height H1 and the second height H2 is calculated by the control circuit 9'.

Thereafter, the control circuit 9' compares the difference with a predetermined reference value S to see if the difference is greater (or smaller) than the reference value S. If the difference is greater than S, it means that the first bonding has not been properly performed, so that the metal wire 10' may readily be detached from the semiconductor chip 3'. Thus, when the difference is found to be greater than the reference value S, an alarm may be sounded to inform the operator of the presence of the defective semiconductor device, and/or the subsequent bonding procedure may be canceled.

On the other hand, if the difference is equal to or less than S, it means that the first bonding has been properly performed so that the metal wire 10' is firmly fixed to the semiconductor chip 3'. In this case, the wire-bonding operation proceeds to the second bonding step as originally scheduled.

The above reference value S may be determined experimentally. In this connection, the inventor of the present invention performed some experiments, and found that the reference value S should be substantially equal to the radius of the metal wire 10'. Of course, the reference value S may be rendered greater or smaller than the radius of the metal wire 10' depending on applications.

In the first and second embodiments described above, wire-bonding operation is performed for connecting a semiconductor chip to leads of the lead frame. Such an example, however, is not limitative. The present invention may be applicable to wire-bonding for connecting a semiconductor chip to a wiring pattern formed on an insulating substrate, for example.

The present invention being thus described, it is obvious that the same may be varied in many other ways. Such variations should not be regarded as a departure from the spirit and scope of the present invention, and all such modifications as would be obvious to those skilled in the art are intended to be included within the scope of the following claims.

What is claimed is:

1. A method of checking a wirebond condition produced by bonding a conductive wire to an object, the method comprising the steps of:

detecting a first position of the object when the wire is brought into contact with the object;

detecting a second position of the object when the bonding of the wire is completed;

calculating a difference between the first and the second positions of the object; and comparing the calculated difference with a predetermined value.

2. The method according to claim 1, further comprising the step of sounding an alarm when the calculated difference is greater than the predetermined value.

3. The method according to claim 1, further comprising the step of canceling a subsequent bonding operation when the calculated difference is greater than the predetermined value.

4. The method according to claim 1, wherein the wire is guided by a bonding tool through which the wire extends.

5. A method of checking a wirebond condition produced by bonding a conductive wire to an object, the wire being held and supplied by a bonding tool, the method comprising the steps of:

detecting a first position of the bonding tool when the wire is brought into contact with the object;

detecting a second position of the bonding tool when the bonding of the wire is completed;

calculating a difference between the first and the second positions of the bonding tool; and comparing the calculated difference with a predetermined value.

6. The method according to claim 5, further comprising the step of sounding an alarm when the calculated difference is greater than the predetermined value.

7. The method according to claim 5, further comprising the step of canceling a subsequent bonding operation when the calculated difference is greater than the predetermined value.

* * * * *